United States Patent
Karunasiri

(10) Patent No.: US 11,121,586 B2
(45) Date of Patent: Sep. 14, 2021

(54) SYSTEMS AND METHODS FOR WIRELESSLY TRANSMITTING POWER AND DATA TO AN IMPLANTABLE STIMULATOR

(71) Applicant: Advanced Bionics AG, Staefa (CH)

(72) Inventor: R. Tissa Karunasiri, Valencia, CA (US)

(73) Assignee: Advanced Bionics AG, Staefa (CH)

(*) Notice: Subject to any disclaimer, the term of this patent is extended or adjusted under 35 U.S.C. 154(b) by 248 days.

(21) Appl. No.: 16/536,760

(22) Filed: Aug. 9, 2019

(65) Prior Publication Data

US 2019/0372405 A1 Dec. 5, 2019

Related U.S. Application Data

(63) Continuation of application No. 15/995,099, filed on May 31, 2018, now Pat. No. 10,418,862.

(51) Int. Cl.
*H04R 25/00* (2006.01)
*H02J 50/80* (2016.01)
(Continued)

(52) U.S. Cl.
CPC .......... *H02J 50/80* (2016.02); *A61N 1/36038* (2017.08); *A61N 1/3787* (2013.01); *A61N 1/37252* (2013.01); *G01R 23/02* (2013.01); *G06F 1/04* (2013.01); *H01Q 1/248* (2013.01); *H02J 7/025* (2013.01); *H02J 50/27* (2016.02);
(Continued)

(58) Field of Classification Search
CPC .. H04R 25/552; H04R 25/554; H04R 25/558; H04S 2400/01; H04S 2420/01; H04S 5/00
See application file for complete search history.

(56) References Cited

U.S. PATENT DOCUMENTS 5,991,664 A 11/1999 Seligman
2006/0190059 A1 8/2006 Griffith
(Continued)

OTHER PUBLICATIONS

"International Search Report and Written Opinion received in International Application No. PCT/US2019/034596, dated Oct. 24, 2019."

*Primary Examiner* — Amir H Etesam
(74) *Attorney, Agent, or Firm* — ALG Intellectual Property, LLC

(57) ABSTRACT

A system includes an interface assembly and electronic circuitry. The interface assembly is configured to receive DC power and a self-clocking differential signal comprising a data signal encoded with a clock signal at a clock frequency. The electronic circuitry is configured to recover, from the self-clocking differential signal, the data signal and the clock signal at the clock frequency, and to generate, based on the recovered clock signal at the clock frequency, a first synthesized clock signal at a first carrier frequency and a second synthesized clock signal at a second carrier frequency. The electronic circuitry is also configured to wirelessly transmit AC power and a data-modulated AC signal to an implantable stimulator implanted within a patient. The AC power is at the first carrier frequency and based on the DC power, while the data-modulated AC signal is at the second carrier frequency and based on the recovered data signal.

20 Claims, 8 Drawing Sheets

(51) Int. Cl.
  *H02J 50/27* (2016.01)
  *H04R 1/10* (2006.01)
  *H01Q 1/24* (2006.01)
  *G01R 23/02* (2006.01)
  *H02J 7/02* (2016.01)
  *A61N 1/378* (2006.01)
  *A61N 1/372* (2006.01)
  *G06F 1/04* (2006.01)
  *A61N 1/36* (2006.01)
  *A61F 2/18* (2006.01)
  *A61N 1/02* (2006.01)

(52) U.S. Cl.
  CPC ........... *H04R 1/1025* (2013.01); *H04R 25/70* (2013.01); *A61F 2/18* (2013.01); *A61F 2002/183* (2013.01); *A61N 1/025* (2013.01); *A61N 1/3727* (2013.01)

(56) References Cited

U.S. PATENT DOCUMENTS

| | | |
|---|---|---|
| 2011/0150255 A1 | 6/2011 | Solum |
| 2011/0208329 A1 | 8/2011 | Castor-Perry |
| 2016/0375243 A1 | 12/2016 | Roehrlein et al. |
| 2017/0028199 A1 | 2/2017 | Roehrlein et al. |
| 2017/0189694 A1* | 7/2017 | Palmer ............... A61N 1/36038 |
| 2017/0244495 A1 | 8/2017 | Ouzounov |
| 2017/0246462 A1 | 8/2017 | Meskens |
| 2018/0050198 A1 | 2/2018 | Mazanec |

* cited by examiner

SYSTEMS AND METHODS FOR WIRELESSLY TRANSMITTING POWER AND DATA TO AN IMPLANTABLE STIMULATOR

RELATED APPLICATIONS

The present application is a continuation application of U.S. patent application Ser. No. 15/995,099, filed May 31, 2018, and entitled "Systems and Methods for Wirelessly Transmitting Power and Data from an Active Headpiece to a Cochlear Implant," which application is incorporated herein by reference in its entirety.

BACKGROUND INFORMATION

Conventional cochlear implant systems include an external sound processor that provides power and data to an implanted cochlear implant by way of a passive headpiece communicatively coupled with the cochlear implant. For example, the sound processor may be worn behind an ear of a patient and may include components such as a battery, a microphone, sound processing circuitry, and wireless transmission circuitry. The sound processor may transmit data-modulated AC power through the skin of the patient to the cochlear implant by way of an antenna coil embedded within a headpiece that is separate from and connected by way of a cable to the sound processor (e.g., a headpiece that is attached to the head at a location that is more closely aligned with the cochlear implant).

Unfortunately, in some examples, there may be certain drawbacks to transmitting power and data from the sound processor to a passive headpiece in this manner. For example, unwanted emissions emanating from the cable between the sound processor and the headpiece may cause emission compliance issues and may be a source of inefficiency compromising the battery life of the cochlear implant system. Additionally, this conventional power and data transmission paradigm may not be particularly flexible. For example, in order for a sound processor to function properly with a given cochlear implant (e.g., including previously-implanted legacy cochlear implants), the sound processor must be capable of providing the data-modulated AC power at a carrier frequency with which the cochlear implant is compatible. Such requirements may place undesirable constraints on sound processor designs.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
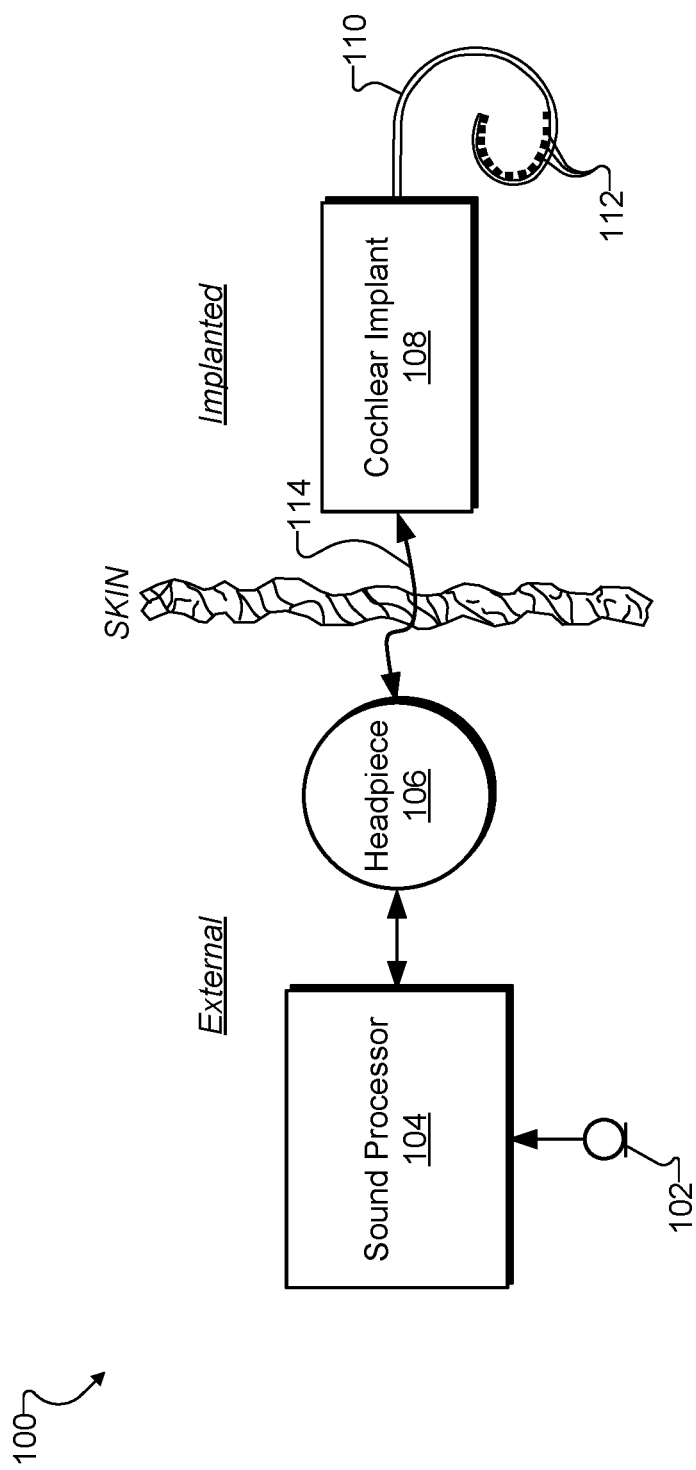
FIG. 1 illustrates an exemplary cochlear implant system according to principles described herein.

Systems and methods for wirelessly transmitting power and data from an active headpiece to a cochlear implant are described herein. In contrast with conventional passive headpieces such as those described above, which may include a passive coil antenna and a network of passive components (e.g., capacitors, inductors, transformers, etc.), an "active headpiece," as used herein, may further include active (i.e., powered) components and circuitry as may serve a particular implementation.

For example, an exemplary active headpiece within a cochlear implant system associated with a patient may include a housing within which is disposed an interface assembly and active electronic circuitry (e.g., power supplies, logic chips, integrated circuits, wireless transmitters, etc.) configured to perform various operations using power received from a sound processor. The housing may be configured to be located external to the patient and may be separate from a housing of the sound processor and/or other such components of the cochlear implant system. For example, the housing of the active headpiece may be configured to be located on the patient's head (e.g., held in place by a magnet) near an implantation site at which the cochlear implant is disposed, while the sound processor may be worn behind the patient's ear or otherwise carried on the patient's body.

The interface assembly disposed within the housing of the headpiece may be communicatively coupled, by way of a cable, to the sound processor included within the cochlear implant system. As such, the interface assembly may be configured to receive, from the sound processor by way of the cable, direct current ("DC") power and a self-clocking differential signal. The self-clocking differential signal may comprise a data signal encoded with a clock signal at a clock frequency. For example, the data signal may be representative of data configured for use by a cochlear implant that is included within the cochlear implant system and is implanted within the patient.

The electronic circuitry disposed within the housing of the headpiece may include any suitable active and/or passive circuitry configured to perform operations described herein. For example, the electronic circuitry may be configured to recover, from the self-clocking differential signal, the data signal and the clock signal at the clock frequency. Based on the recovered clock signal at the clock frequency, the electronic circuitry may further generate a first synthesized clock signal at a first carrier frequency and a second synthesized clock signal at a second carrier frequency. For example, at least one of the first and second carrier frequencies may be distinct from the clock frequency of the recovered clock signal. Based on the synthesized clock signals, the electronic circuitry may wirelessly transmit alternating current ("AC") power and data to the cochlear implant through the skin of the patient. For example, based on the DC power, the electronic circuitry may wirelessly transmit AC power at the first carrier frequency. Additionally, based on the recovered data signal, the electronic circuitry may wirelessly transmit a data-modulated AC signal at the second carrier frequency.

Systems and methods for wirelessly transmitting power and data from an active headpiece to a cochlear implant described herein may provide various benefits. For example, when AC power and data generated by components within the active headpiece (as opposed to being generated by a sound processor connected to the headpiece by way of a cable) are transmitted directly from the active headpiece to the cochlear implant as described herein, efficiency may be increased and emissions decreased as compared to conventional configurations in which AC power and data are transmitted to the cochlear implant from a sound processor by way of a passive headpiece. Specifically, when AC power and data are generated at the sound processor and transmitted by way of a cable (e.g., a coaxial cable) to be radiated by an antenna coil of a passive headpiece, unwanted emissions may radiate out of the cable, causing power to be lost (i.e., thereby decreasing efficiency) and possibly creating issues for emission compliance requirements. These efficiency and emissions issues may be resolved by sending power and data to an active headpiece in accordance with the systems and methods described herein.

Additionally, by including clock generation circuitry and power and data transmission circuitry within an active headpiece, rather than in the sound processor, sound processor design may be streamlined to provide users with smaller and less bulky sound processors. A great degree of flexibility may also be provided by the systems and methods described herein. For example, because active headpieces described herein may recover clock signals at one frequency and then generate synthesized clock signals at other, different frequencies, various sound processors and cochlear implants may be able to operate compatibly with one another using the active headpieces where they may have been incompatible otherwise (e.g., due to clock frequencies, voltage levels, etc.). As will be described in more detail below, one or more AC signals (e.g., for power and/or data) may be exchanged between cochlear implants and active headpieces disclosed herein at reconfigurable clock frequencies that may be conveniently set up and modified using software (e.g., by writing registers within the active headpiece), rather than requiring updates to hardware.

Various embodiments will now be described in more detail with reference to the figures. The disclosed methods and systems may provide one or more of the benefits mentioned above and/or various additional and/or alternative benefits that will be made apparent herein.

In order to illustrate the context within which systems and methods for wirelessly transmitting power and data from an active headpiece to a cochlear implant may be employed, a cochlear implant system will now be described.

Specifically, FIG. 1 shows an exemplary cochlear implant system 100. As shown, cochlear implant system 100 may include various components configured to be located external to a cochlear implant patient (i.e., a user of the cochlear implant system) including, but not limited to, a microphone 102, a sound processor 104, and a headpiece 106. Cochlear implant system 100 may further include various components configured to be implanted within the patient including, but not limited to, a cochlear implant 108 (also referred to as an implantable cochlear stimulator) and a lead 110 (also referred to as an intracochlear electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a microphone such as a T-MIC™ microphone from Advanced Bionics. Microphone 102 may be associated with a particular ear of the patient such as by being located in a vicinity of the particular ear (e.g., within the concha of the ear near the entrance to the ear canal). In some examples, microphone 102 may be held within the concha of the ear near the entrance of the ear canal by a boom or stalk that is attached to an ear hook configured to be selectively attached to sound processor 104. Additionally or alternatively, microphone 102 may be implemented by one or more microphones disposed within sound processor 104, one or more microphones disposed within headpiece 106, and/or any other suitable microphone or microphones as may serve a particular implementation.

Sound processor 104 may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway of the patient such as an auditory nerve of the patient. Exemplary stimulation sites include, but are not limited to, one or more locations within the cochlea, the cochlear nucleus, the inferior colliculus, and/or any other nuclei in the auditory pathway. While, for the sake of simplicity, electrical stimulation will be described herein as being applied to one or both of the cochleae of a patient, it will be understood that stimulation current may also be applied to other suitable nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. In some examples, sound processor 104 may be implemented by an electro-acoustic stimulation ("EAS") sound processor included in an EAS system configured to provide electrical and acoustic stimulation to a patient.

Sound processor 104 may wirelessly transmit power and/or stimulation parameters (e.g., in the form of data words included in a forward telemetry sequence) to cochlear implant 108 by way of a wireless communication link 114 between headpiece 106 and cochlear implant 108. It will be understood that communication link 114 may include a bidirectional communication link and/or one or more dedicated unidirectional communication links. In the same or other examples, sound processor 104 may transmit (e.g., wirelessly transmit) information such as an audio signal detected by microphone 102 to another sound processor (e.g., a sound processor associated with another ear of the patient). For example, as will be described in more detail below, the information may be transmitted to the other sound processor by way of a wireless audio transmission link (not explicitly shown in FIG. 1).

Headpiece 106 may be separate from sound processor 104 (i.e., disposed in a separate housing from the housing of sound processor 104), but may be communicatively coupled to sound processor 104 by way of a cable including one or more conductors. For instance, in conventional cochlear implant systems in which headpiece 106 is implemented as a passive headpiece, the cable may be a coaxial cable configured to carry AC power and data signals generated at sound processor 104 to be radiated from an antenna coil disposed within headpiece 106. Conversely, in cochlear implant system implementations, such as described herein, in which headpiece 106 is implemented as an active headpiece, the cable may include several conductors (e.g., including one or more twisted pairs for carrying a differential signal) for carrying various power and data signals described herein.

Regardless of whether headpiece 106 is implemented as a passive or an active headpiece, headpiece 106 may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via communication link 114.

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104 by way of headpiece 106. Cochlear implant 108 may be further configured to apply the electrical stimulation to one or more stimulation sites within the patient via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") by way of multiple electrodes 112.

Figure 2:
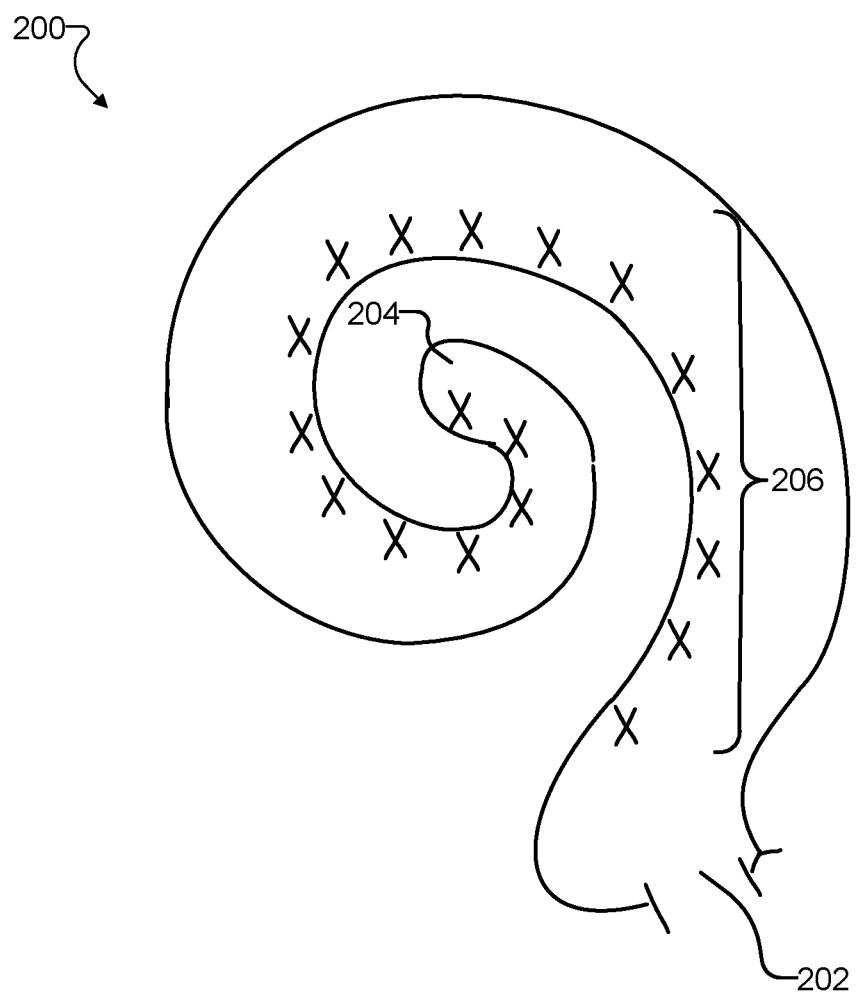
FIG. 2 illustrates a schematic structure of the human cochlea according to principles described herein.

FIG. 2 illustrates a schematic structure of a human cochlea 200 into which lead 110 may be inserted. As shown in FIG. 2, cochlea 200 is in the shape of a spiral beginning at a base 202 and ending at an apex 204. Within cochlea 200 resides auditory nerve tissue 206, which is denoted by $X_S$ in FIG. 2. Auditory nerve tissue 206 is organized within cochlea 200 in a tonotopic manner. That is, relatively low frequencies are encoded at or near apex 204 of cochlea 200 (referred to as an "apical region") while relatively high frequencies are encoded at or near base 202 (referred to as a "basal region"). Hence, each location along the length of cochlea 200 corresponds to a different perceived frequency. Cochlear implant system 200 may therefore be configured to apply electrical stimulation to different locations within cochlea 200 (e.g., different locations along auditory nerve tissue 206) to provide a sensation of hearing to the patient. For example, when lead 110 is properly inserted into cochlea 200, each of electrodes 112 may be located at a different cochlear depth within cochlea 200 (e.g., at a different part of auditory nerve tissue 206) such that stimulation current applied to one electrode 112 may cause the patient to perceive a different frequency than the same stimulation current applied to a different electrode 112 (e.g., an electrode 112 located at a different part of auditory nerve tissue 206 within cochlea 200).

Figure 3:
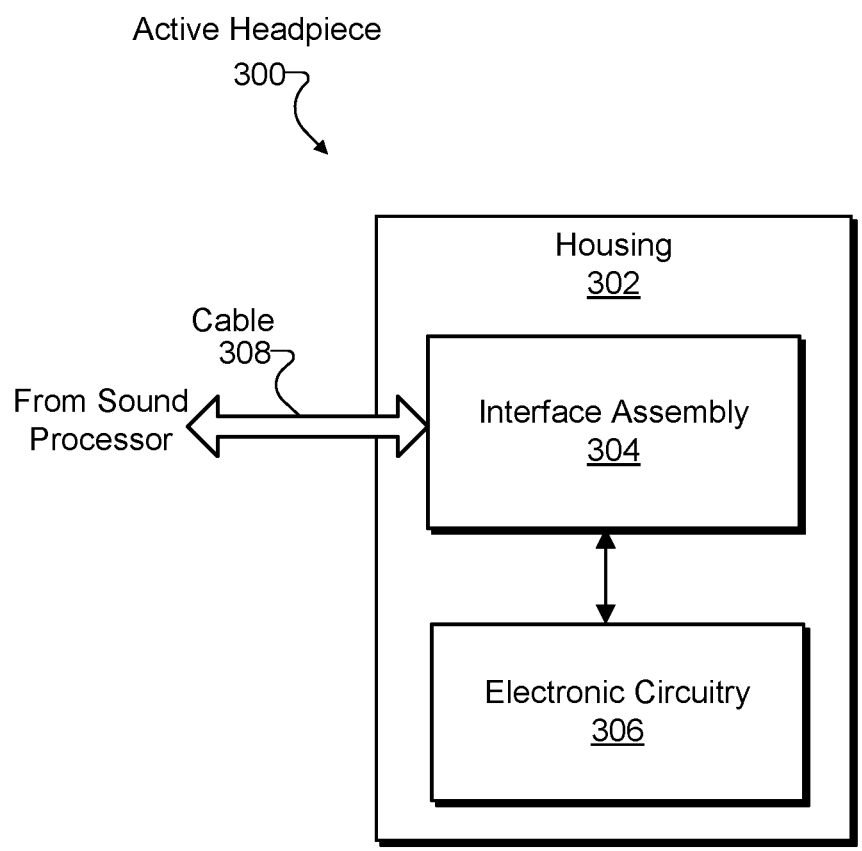
FIG. 3 illustrates an active headpiece included within a cochlear implant system and configured to wirelessly transmit power and data to a cochlear implant according to principles described herein.

FIG. 3 illustrates an active headpiece 300 that may be included within a cochlear implant system such as cochlear implant system 100 and may be configured to wirelessly transmit power and data to a cochlear implant according to principles described herein. As shown, active headpiece 300 may include, without limitation, a housing 302, an interface assembly 304, and electronic circuitry 306. Interface assembly 304 and electronic circuitry 306 may be communicatively coupled to one another and may be disposed (i.e., housed) within housing 302. For example, interface assembly 304 and electronic circuitry 306 may be "disposed within" housing 302, as that term is used herein, if the components comprising interface assembly 304 and electronic circuitry 306 are at least partially contained inside housing 302. In some examples, housing 302 may completely enclose all of the components of interface assembly 304 and/or electronic circuitry 306, whereas, in other examples, at least one component of interface assembly 304 or electronic circuitry 306 may be only partially housed within housing 302 (e.g., such as a connector that protrudes through a wall of housing 302).

Interface assembly 304 may include any connectors, conductors, pads, passive electrical components, active electrical components, mechanical components, and/or other suitable components configured to facilitate active headpiece 300 in exchanging electrical power and/or data with a sound processor (not explicitly shown in FIG. 3) that is communicatively coupled with interface assembly 304 by way of a cable 308. The sound processor may be further included within the cochlear implant system in which active headpiece 300 is included, but may be external to housing 302. For example, the sound processor may be a completely separate system component from active headpiece 300 within the cochlear implant system, and may be disposed within a dedicated housing of its own that is separate from housing 302.

Interface assembly 304 may be configured to exchange any power and/or data signals with the sound processor over cable 308 as may serve a particular implementation. For example, interface assembly 304 may receive DC power from the sound processor over cable 308. Additionally, interface assembly 304 may receive, over cable 308, a self-clocking differential signal comprising a data signal encoded with a clock signal at a clock frequency. The data signal may be representative of data configured for use by a cochlear implant (e.g., cochlear implant 108).

Electronic circuitry 306 may receive the DC power, the self-clocking differential signal, and/or other power or data signals provided by the sound processor by way of interface assembly 304. Upon receiving the power and data signals, electronic circuitry 306 may be configured to recover the data signal and the clock signal from the self-clocking differential signal and to generate, based on the recovered clock signal, a first synthesized clock signal at a first carrier frequency and a second synthesized clock signal at a second carrier frequency. The first and second carrier frequencies at which the first and second synthesized clock signals are generated may be any suitable frequencies generated in any suitable way, as will be described below. For example, at least one of the first and second carrier frequencies may be distinct from the clock frequency of the recovered clock signal. Having recovered the data signal and the clock signal, electronic circuitry 306 may wirelessly transmit AC power to the cochlear implant based on the DC power and at the first carrier frequency (e.g., using the first synthesized clock signal as a clock for the wireless transmission). Additionally, electronic circuitry 306 may wirelessly transmit a data-modulated AC signal to the cochlear implant based on the recovered data signal and at the second carrier frequency (e.g., using the second synthesized clock signal as a clock for the wireless transmission).

In some examples, along with receiving data signals from the sound processor, electronic circuitry 306 may also provide data signals to the sound processor. For example, as will be described in more detail below, a back-telemetry data signal may be received from the cochlear implant over a wireless link between active headpiece 300 and the cochlear implant. The back-telemetry data signal may be received by active headpiece 300 and sent to the sound processor over cable 308.

Figure 4:
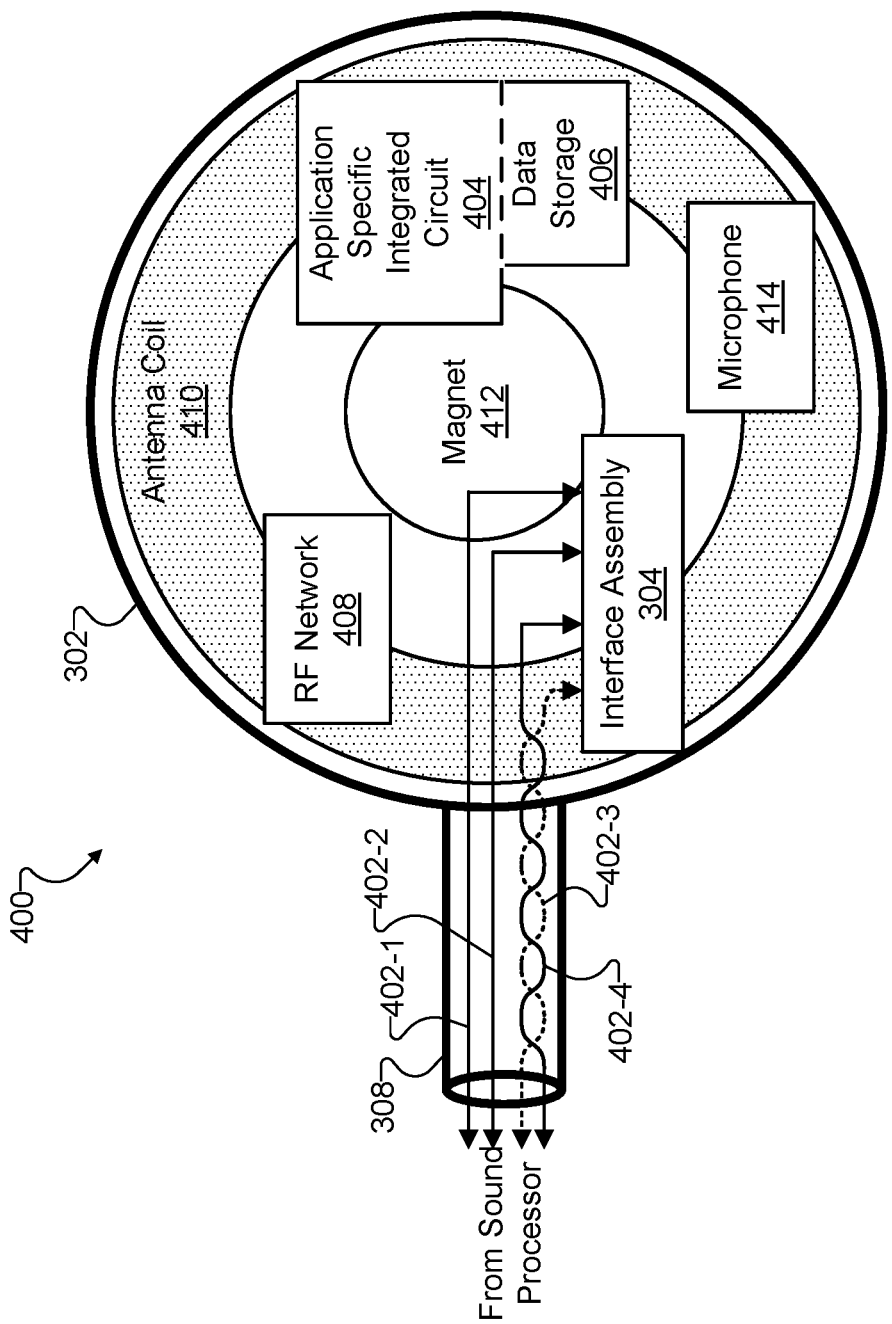
FIG. 4 illustrates an exemplary implementation of the active headpiece of FIG. 3 according to principles described herein.

FIG. 4 illustrates an exemplary implementation 400 of active headpiece 300. It will be understood that implementation 400 illustrates just one particular way that an active headpiece for wirelessly transmitting power and data to a cochlear implant may be implemented. As such, implementation 400 may be modified in various ways (e.g., ways described herein or any other suitable way) to create other suitable implementations of active headpiece 300. For example, additional or fewer components as shown in implementation 400 may be used in various other implementations of active headpiece 300.

As shown within cable 308, a plurality of conductors 402 (e.g., conductors 402-1 through 402-4) may be included within implementation 400 for exchanging power and/or data signals between a sound processor (not explicitly shown in FIG. 4) and interface assembly 304. Interface assembly 304 is shown to be disposed within housing 302 (e.g., implemented as a circular housing within implementation 400) along with various electronic circuitry and other components also disposed within the housing. For example, as shown, housing 302 further encloses an application specific integrated circuit ("ASIC") 404 associated with a data storage facility 406, a radio frequency ("RF") network 408, an antenna coil 410, a magnet 412, and a microphone 414. While explicit connections among these other components are not explicitly illustrated, it will be understood that the electronic elements housed within housing 302 may be selectively and communicatively coupled with one another in any manner as may serve a particular implementation so as to be able to perform operations described herein.

Conductors 402 may be implemented as wires or other suitable conductors enclosed within an insulative casing of cable 308. In some examples, a 4-wire interface between the sound processor and active headpiece 300 may be employed that includes the four conductors 402 illustrated in FIG. 4. In other examples, additional conductors beyond conductors 402 of the 4-wire interface may also be used. Conductor 402-1 may be used to carry DC power from the sound processor to active headpiece 300 and/or to carry an electrical signal (e.g., a back-telemetry data signal, a microphone signal, etc.) from active headpiece 300 back to the sound processor. Conductor 402-2 may be used in conjunction with conductor 402-1 to serve as a ground reference. Conductors 402-3 and 402-4 may be implemented by a twisted pair of wires so as to facilitate an efficient and low-emission wired transmission of differential signals such as a self-clocking differential signal sent from the sound processor to active headpiece 300. To illustrate, conductors 402-3 and 404-4 are depicted as being twisted around one another throughout cable 308. In other examples, conductors 402 may be implemented in other ways such as using coaxial conductors or the like.

ASIC 404 may include various logic, power supplies, clock generation and/or derivation circuitry (e.g. clock control loops, etc.), and/or other electronic circuitry used to perform the operations described herein. ASIC 404 will be described below in more detail. However, it will be understood that the functionality provided by ASIC 404 (as well as data storage facility 406) may be provided to active headpiece 300 in any suitable manner. For example, rather than being performed within a special-purpose ASIC as will be described below, the functionality of ASIC 404 and/or data storage facility 406 may be performed by discrete components or integrated circuits, by discrete logic circuitry, by a general purpose microprocessor or other computing component, by programmable hardware such as a field programmable gate array ("FPGA"), by a combination thereof, or by any other passive or active electronic circuitry as may serve a particular implementation.

Data storage facility 406 may be associated with ASIC 404 in any suitable way and may be used to store any suitable data. For example, data storage facility 406 may be integrated within (i.e., built into) ASIC 404 in certain implementations, and may be implemented as an external storage device (e.g., a discrete storage device included within housing 302 such as a flash memory device, an EEPROM device, or the like) in other implementations. In implementations in which data storage facility 406 is implemented on a chip separate from ASIC 404, ASIC 404 may include a data storage interface (e.g., a dedicated communication interface) for communicatively coupling ASIC 404 with the external storage device upon which data storage facility 406 is implemented.

Data storage facility 406 may be configured to maintain any data received, generated, managed, maintained, used, and/or transmitted by ASIC 404, active headpiece 300, or the cochlear implant system within which active headpiece 300 is included. For example, data storage facility 304 may hold configuration values for ASIC 404 and the circuitry implemented therein. For instance, register values configuring clock frequencies to be generated and used by active headpiece 300 may be stored in data storage facility 406 and loaded into registers within ASIC 404 upon system startup (e.g., when active headpiece 300 operates in a setup mode as will be described in more detail below). As another example, data storage facility 304 may store data used by the sound processor, such as data (e.g., backup data) representative of sound processing parameters associated with a particular patient, sound processing programs used by the sound processor, or the like.

RF network 408 may include a network of passive components (e.g., capacitors, inductors, transformers, etc.) configured to facilitate antenna coil 410 in transcutaneously exchanging wireless signals with a corresponding antenna coil associated with a cochlear implant implanted within the patient. For example, RF network 408 may include passive electronic circuitry that achieves an effective and efficient impedance for antenna coil 410 in a manner similar to or the same as that employed by conventional passive headpieces.

Antenna coil 410 may be disposed along an outer perimeter of active headpiece 300, as shown. In some examples, antenna coil 410 may represent a single antenna coil comprised within active headpiece 300. In such examples, the electronic circuitry within active headpiece 300 (e.g., ASIC 404, RF network 408, etc.) may wirelessly transmit both AC power at a first carrier frequency and the data-modulated AC signal at the second carrier frequency by way of the single antenna coil represented by antenna coil 410. In other examples, antenna coil 410 may represent both a first antenna coil and a second antenna coil distinct from the first antenna coil, both of which are comprised within active headpiece 300. In these examples, the electronic circuitry within active headpiece 300 may wirelessly transmit the AC power at the first carrier frequency by way of the first antenna coil, and may wirelessly transmit the data-modulated AC signal at the second carrier frequency by way of the second antenna coil. Additionally, one or more additional antenna coils such as an antenna coil dedicated to receiving a back-telemetry wireless signal from the cochlear implant may also be included in the plurality of antenna coils represented by antenna coil 410.

Magnet 412 may be included within active headpiece 302 in the same way and for the same reason as magnets may be included in conventional passive headpieces. Specifically, magnet 412 may be used to align active headpiece 300 with a cochlear implant implanted under the skin of the patient, as well as to hold active headpiece 300 in place on the patient's head. In other examples, other suitable alignment and/or attachment mechanisms or techniques may be employed in addition to or as an alternative to magnet 412.

In certain examples, active headpiece 300 may include microphone 414 to replace or augment the detection of sound performed by one or more microphones disposed in other locations. In examples in which active headpiece 300 includes microphone 414 disposed within housing 410, microphone 414 may be communicatively coupled to the sound processor by way of cable 308. For example, microphone 414 may be configured to detect sound presented to the patient and to generate and provide, to the sound processor by way of one or more of conductors 402 (e.g., an additional conductor 402 not explicitly shown), a signal representative of the sound. In such examples, the data signal representative of data configured for use by the cochlear implant (i.e., the data signal comprised within the self-clocking differential signal received from the sound processor) may be generated by the sound processor based on the signal representative of the sound generated and provided by microphone 414.

While various components that may be included within active headpiece 300 have been illustrated and described in reference to implementation 400, it will also be noted that certain components may be advantageously omitted from certain implementations of active headpiece 300. For example, because electronic circuitry included within active headpiece 300 (e.g., within ASIC 404) may be configured to recover a clock signal received from the sound processor and to generate synthesized clock signals based on the recovered clock signal, no crystal oscillator or other such component may be employed within active headpiece 300 to generate clock signals from scratch. To the contrary, all clock signals generated within and/or used by electronic circuitry in active headpiece 300 may be derived from a clock signal generated by an oscillator included within the sound processor. In like manner, active headpiece 300 may be configured to be powered exclusively by power received from the sound processor, such that no battery may be disposed within housing 302 of active headpiece 300 in certain implementations.

Electronic circuitry within active headpiece 300 may perform any of various operations described herein. As mentioned above, many such operations may be performed by application specific circuitry built into a special purpose chip such as ASIC 404, or by other suitable electronic circuitry. Specifically, for example, ASIC 404 may be configured in certain implementations to receive (e.g., by way of interface assembly 304 from a sound processor external to housing 302) DC power and/or a self-clocking differential signal comprising a data signal encoded with a clock signal at a clock frequency, the data signal representative of data configured for use by a cochlear implant included within the cochlear implant system and configured to be implanted within the patient. ASIC 404 may be further configured to recover, from the self-clocking differential signal, the data signal and the clock signal at the clock frequency. Based on the recovered clock signal at the clock frequency, ASIC 404 may be configured to generate a first synthesized clock signal at a first carrier frequency and a second synthesized clock signal at a second carrier frequency, wherein at least one of the first and second carrier frequencies is distinct from the recovered clock frequency. ASIC 404 may be configured to wirelessly transmit, to the cochlear implant, AC power at the first carrier frequency based on the DC power, and a data-modulated AC signal at the second carrier frequency based on the recovered data signal.

Figure 5:
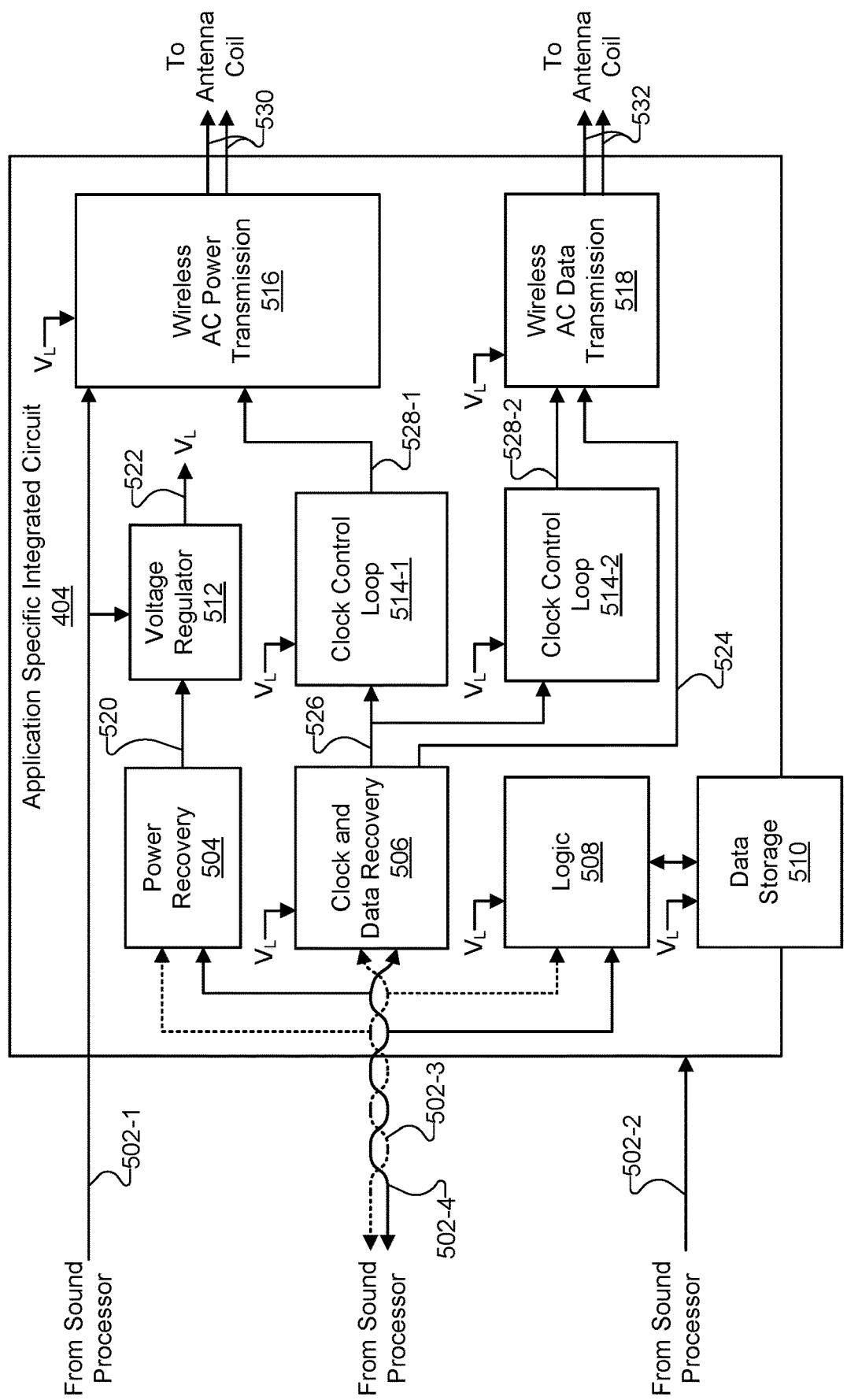
FIG. 5 illustrates an exemplary implementation of an application specific integrated circuit for use within the active headpiece of FIG. 3 according to principles described herein.

To illustrate, FIG. 5 depicts a block diagram of an exemplary implementation of ASIC 404. ASIC 404 may include various inputs, outputs, components, functional blocks, intermediary signals, and so forth, that enable ASIC 404 to perform various operations described herein. For example, as shown, ASIC 404 may receive various inputs 502 (e.g., inputs 502-1 through 502-4) for use by a variety of functional blocks including, without limitation, a power recovery facility 504, a clock and data recovery facility 506, a logic facility 508, a data storage facility 510, a voltage regulator 512, at least two clock control loops 514 (e.g., clock control loops 514-1 and 514-2), a wireless AC power transmission facility 516, a wireless AC data transmission facility 518, and any other facilities, components, etc. as may serve a particular implementation.

Functional blocks 504 through 518 may be implemented in any suitable way, such as by dedicated logic and other hardware built into ASIC 404 (e.g., very-large-scale integration ("VLSI") hardware, mixed signal integrated circuit hardware, system on a chip ("SoC") hardware, mixed signal SoC hardware, etc.). Additionally, each functional block 504 through 518 may be selectively and communicatively coupled to one another in any suitable way, including by way of the connections shown in FIG. 5 or by way of other suitable connections.

Inputs 502 may be received by ASIC 404 from a sound processor by way of interface assembly 304, described above. Specifically, input 502-1 may correspond to (e.g., may be the same as or derived based on) a signal carried by conductor 402-1, input 502-2 may correspond to a signal carried by conductor 402-2, input 502-3 may correspond to a signal carried by conductor 402-3, and input 502-4 may correspond to a signal carried by conductor 402-4. Just as conductors 402-3 and 402-4 may be configured to facilitate proper transmission of a differential signal in the ways described above (e.g., by forming a twisted pair of conductors, etc.), PCB traces around ASIC 404 and/or conduction paths internal to ASIC 404 may be specially configured to carry inputs 502-3 and 502-4 as a differential signal by, for example, being matched in length, impedance, and the like.

Power recovery facility 504 may receive a differential signal (e.g., a self-clocking differential signal) from inputs 502-3 and 502-4 and, based on DC power included within the differential signal, may generate a recovered power 520, which may be a fixed DC power having a voltage that is fixed at a particular level (e.g., 1.0 V). In other words, recovered power 520 may be derived from a self-clocking differential signal received by active headpiece 300 from the sound processor, rather than, for example, from the DC power sent by the sound processor and received by ASIC 400 as input 502-1, or from any internal battery or other power source within active headpiece 300.

During normal operation, when the cochlear implant system is providing stimulation to the patient to invoke the sensation of hearing, recovered power 520 may be used by voltage regulator 512 to derive a logic power 522 (abbreviated in FIG. 5 as "$V_L$" for "$V_{Logic}$"). As shown, logic power 522 may be used throughout ASIC 404 to power some or all of the other facilities and functional blocks within ASIC 404. As such, in these examples, ASIC 404 may use the fixed DC power of recovered power 520 to perform the recovery of the data signal and the clock signal and to perform the generation of the first and second synthesized clock signals.

Voltage regulator 512 may be implemented by any suitable type of voltage regulator (e.g., a linear regulator such as a linear drop-out ("LDO") regulator, a switching regulator, a hybrid regulator, etc.) configured to generate logic power 522 as a clean and stable power rail. As described above, voltage regulator 512 may generate logic power 522 based on recovered power 520 in certain examples (e.g., during normal operation). In other examples, however, voltage regulator 512 may generate logic power 522 based on the DC power sent by the sound processor and received as input 502-1. Thus, as shown, input 502-1 may also be connected as an input to voltage regulator 512 along with recovered power 520 so that voltage regulator 512 may opt to use either or both power sources in different implementations or when operating in different modes.

During normal operation, the DC power coming in on input 502-1 may be variable DC power having a variable voltage level that changes, for example, based on a sound level being picked up by a microphone in the cochlear implant system. For instance, the DC power coming in on input 502-1 may be 0.5 V when the patient is in a relatively quiet location, or 3.0 V when the patient is in a relatively noisy location. This wide variability in the DC power of input 502-1 during normal operation may make it difficult or impractical for logic power 522 to be derived from the variable DC power, particularly if the desired voltage level for logic power 522 is within the range across which the variable DC power varies (e.g., as 1.0 V is within the range of 0.5 V to 3.0 V). For this reason, it may be convenient, although not required, for voltage regulator 512 to use recovered power 520 to generate logic power 522 during normal operation of the cochlear implant system. However, when the cochlear implant system is in modes of operation other than the normal mode of operation (e.g., a setup mode of operation), the DC power coming in on input 502-1 from the sound processor may have a narrower range, or may be a fixed DC power having a voltage that is fixed at a particular level. As such, particularly in these other modes of operation, voltage regulator 512 may use the fixed DC power on input 502-1 to generate logic power 522 for performing the recovery of the data signal and the clock signal and performing the generation of the first and second synthesized clock signals. In still other examples, a battery included within active headpiece 300 may be used to generate power from which voltage regulator 512 may derive logic power 522.

Just as power recovery facility 504 recovers power from a self-clocking differential signal coming in on inputs 502-3 and 502-4, clock and data recovery facility 506 may also be configured to perform a recovery operation from the self-clocking differential signal sent by the sound processor on these inputs. However, rather than recovering power, clock and data recovery facility 506 may recover a data signal 524 and a clock signal 526 that is encoded with data signal 524 using a particular encoding technique used by the sound processor. For example, data signal 524 may have been encoded with clock signal 526 using a Manchester clock encoding technique, and clock and data recovery facility 506 may be configured to recover data signal 524 and clock signal 526 in accordance with the Manchester clock encoding technique. As another example, data signal 524 may have been encoded with clock signal 526 using a biphase-mark clock encoding technique, and clock and data recovery facility 506 may be configured to recover data signal 524 and clock signal 526 in accordance with the biphase-mark clock encoding technique. In still other examples, various other established or proprietary clock encoding schemes (e.g., differential Manchester encoding, other types of biphase encoding, etc.) may be employed as may serve a particular implementation. Clock and data recovery facility 506 may operate using a clock control loop such as a phase-locked loop ("PLL"), a delay-locked loop ("DLL"), or any other suitable clock recovery circuit used to decode self-clocking differential signals based on the encoding scheme with which they are encoded.

Clock control loops 514 may also be implemented using PLLs, DLLs, and/or other suitable clock control loops configured to synthesize clock signals at programmable clock frequencies (e.g., arbitrary clock frequencies, clock frequencies within a particular range, etc.) that may be different from a clock frequency of an input signal used to synthesize the clock signals. For example, if clock signal 526 has a clock frequency of 1.0 MHz, clock control loop 514-1 may synthesize a clock signal 528-1 at a clock frequency of 5.0 MHz while clock control loop 514-2 may synthesize a clock signal 528-2 at a clock frequency of 49.0 MHz. In other examples, at least one of synthesized clock signals 528 may have the same clock frequency as recovered clock signal 526 and/or may have a lower clock frequency than that of recovered clock signal 526.

Clock control loops 514 may be programmable by writing registers or otherwise setting values associated with the clock control loop circuitry to define the expected clock frequency of the input clock signal (i.e., clock signal 526) and the desired clock frequency of the output clock signal (i.e., clock signals 528-1 or 528-2). Values for such registers may be stored within data storage 510. As such, the values may be set to the registers, as well be read from and/or written (e.g., overwritten, reprogrammed, etc.) to data storage 510, when active headpiece 300 is in a setup mode of operation (e.g., at startup and/or before shutting down).

In this way, active headpiece 300 may provide a large amount of flexibility for compatibility with a wide variety of different sound processors and/or cochlear implants configured to operate at different clock frequencies. For example, a particular sound processor configured to generate a self-clocking differential signal at a first particular clock frequency may be made to be compatible with various cochlear implants configured to receive power and/or data transmissions on various different carrier frequencies by properly configuring clock control loops 514 in software (e.g., by properly writing the appropriate registers) without any change in hardware (e.g., such as replacing one crystal oscillator with another). As another example, a particular cochlear implant configured to receive power and/or data transmissions at a particular carrier frequency (or plurality of carrier frequencies) may be made to be compatible with various sound processors configured to generate self-clocking differential signals at different clock frequencies by similarly configuring clock control loops 514.

As shown, clock signal 528-1 may be used by wireless AC power transmission facility 516 as a carrier frequency for a power transmission output 530, while clock signal 528-2 may be used by wireless AC data transmission facility 518 as a carrier frequency for a data transmission output 532. For example, outputs 530 and 532 may be implemented as RF signals that may carry a significant amount of power (e.g., power sufficient to power the cochlear implant) and/or may include modulated data. As such, clock signals 528 may each be implemented with any clock frequency as may serve as a suitable power carrier frequency (for wireless AC power transmission facility 516) or a suitable data carrier frequency (for wireless AC data transmission facility 518) in a particular implementation. For instance, in some examples, the clock frequency of clock signals 528 may be programmed to a frequency upon which emission regulations (e.g., FCC regulations in the United States) allow cochlear implant systems to transmit.

It may be advantageous, in certain examples, for the clock frequency of clock signal 528-2 (i.e., the carrier frequency at which data output 532 is to be transmitted) to be programmed to be significantly higher (e.g., at least twice as high) as the clock frequency of clock signal 528-1 (i.e., the carrier frequency at which power output 530 is to be transmitted). For example, data at a particular clock rate (e.g., the clock rate of clock signal 526) may best be modulated onto a carrier signal when the carrier frequency of the carrier signal is significantly faster than the rate at which the data is clocked. As such, it may be desirable for the carrier frequency of data output 532 to be relatively high. Because this transmission may use a relatively low voltage and low power, it may be relatively efficient to employ the high carrier frequency. In contrast, for power output 530, it may be much more important, for the sake of efficiency, for the carrier frequency to be relatively low. For example, switching power consumed by wireless AC power transmission facility 516 may be significantly reduced by driving power output 530 at a relatively low carrier frequency. Additionally, power output 530 may be tuned with a large quality factor ("Q factor") so as to oscillate efficiently because of the fact that power and data are sent by active headpiece 300 separately at different frequencies, rather than by modulating the data onto the power signal.

As shown, wireless AC power transmission 516 may generate power output 530 based on the DC power coming into ASIC 404 on input 502-1. As mentioned above, this DC power may be a variable DC power that changes based on the sound level experienced by the patient in whatever environment the patient is in (at least when operating in the normal operation mode). Accordingly, it will be understood that power output 530 may provide a variable amount of power to the cochlear implant while data output 532 may be generated at a fixed voltage.

Logic facility 508 may represent any logic circuitry included within ASIC 404 that has not already been described as part of one of the other facilities. Logic facility 508 may perform various functions including, for example, interfacing with data storage facility 510. Data storage facility 510 may implement data storage facility 406 (described above) and, as such, may be an integrated data storage facility built into ASIC 404 in some examples, and an external data storage facility with which ASIC 404 (e.g., logic facility 508) is configured to interface and communicate in other examples. For instance, logic facility 508 may be configured to provide read/write access to the sound processor when active headpiece 300 is in a setup mode of operation, and to make data storage facility 510 transparent to the sound processor when active headpiece 300 is in a normal mode of operation.

Figure 6:
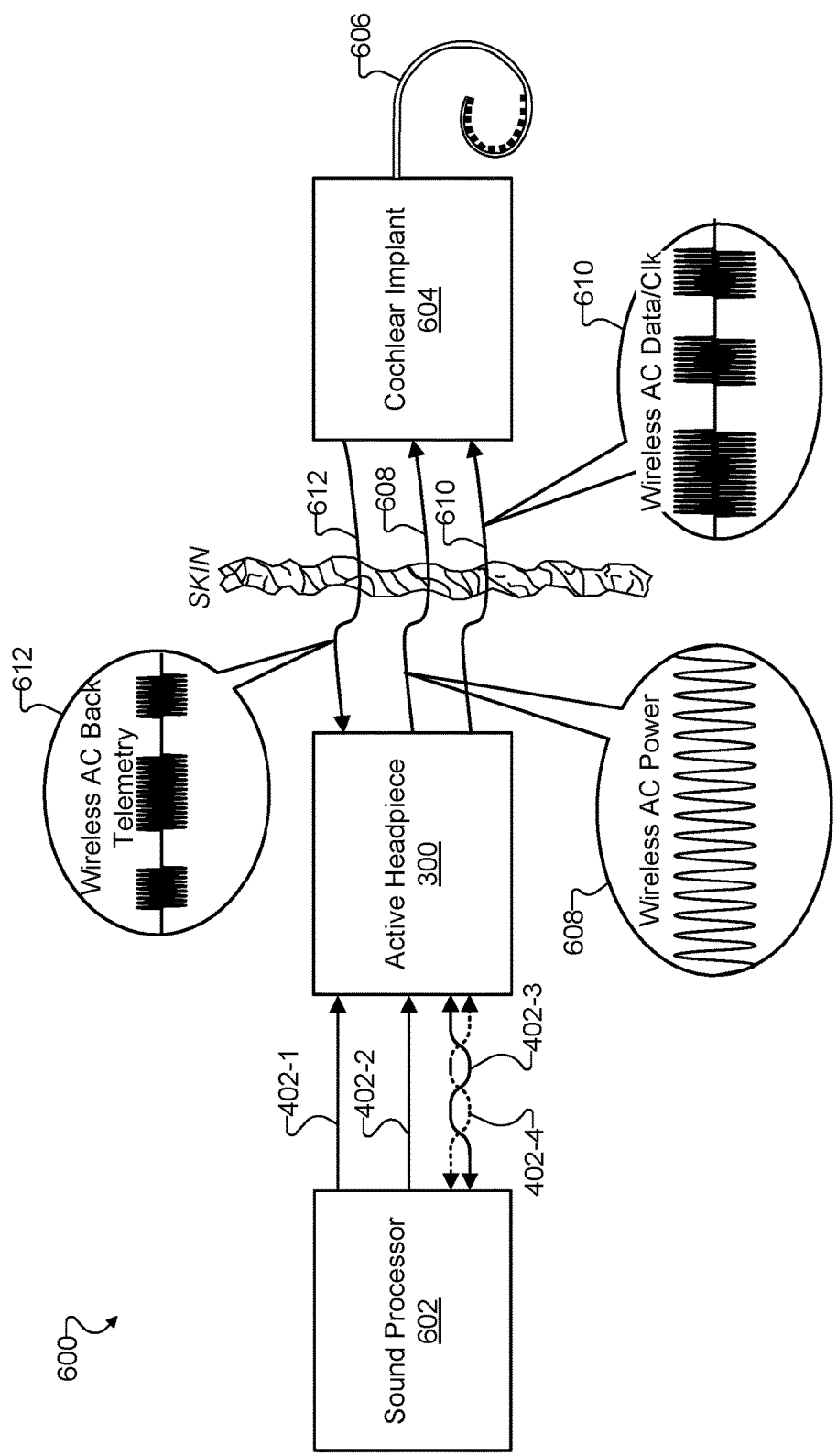
FIG. 6 illustrates an exemplary configuration in which the active headpiece of FIG. 3 interoperates with a sound processor and a cochlear implant within an exemplary cochlear implant system according to principles described herein.

FIG. 6 illustrates an exemplary configuration 600 in which active headpiece 300 interoperates with a sound processor 602 and a cochlear implant 604 within an exemplary cochlear implant system. The cochlear implant system comprising the components of configuration 600 may be similar to cochlear implant system 100, described above. For example, sound processor 602 may be analogous to sound processor 104, cochlear implant 604 may be analogous to cochlear implant 108, and a lead 606 coupled with cochlear implant 604 may be analogous to lead 110. In configuration 600, active headpiece 300 may perform the role described above in relation to headpiece 106. However, unlike headpiece 106, which may be implemented as a passive headpiece, active headpiece 300 is implemented as an active headpiece that is configured to perform the active operations described herein.

As shown in FIG. 6, a 4-conductor interface between sound processor 602 and active headpiece 300, which may be implemented in two separate housings, may be employed. Specifically, conductors 402 may serve to electrically and communicatively couple sound processor 602 to active headpiece 300. As mentioned above, conductors 402 may carry any power and/or data signals as may serve a particular implementation. While, in some examples, conductors 402 may each be dedicated to a single purpose (e.g., to carrying a single type of power or data signal), conductors 402 may, in other examples, be configured to carry different types of power or data signals at different times in accordance with a time domain multiplexing scheme. For instance, in some implementations, at least two modes of operation may be defined for the cochlear implant system, and conductors 402 may have distinct purposes in the different modes of operation.

Figure 7:
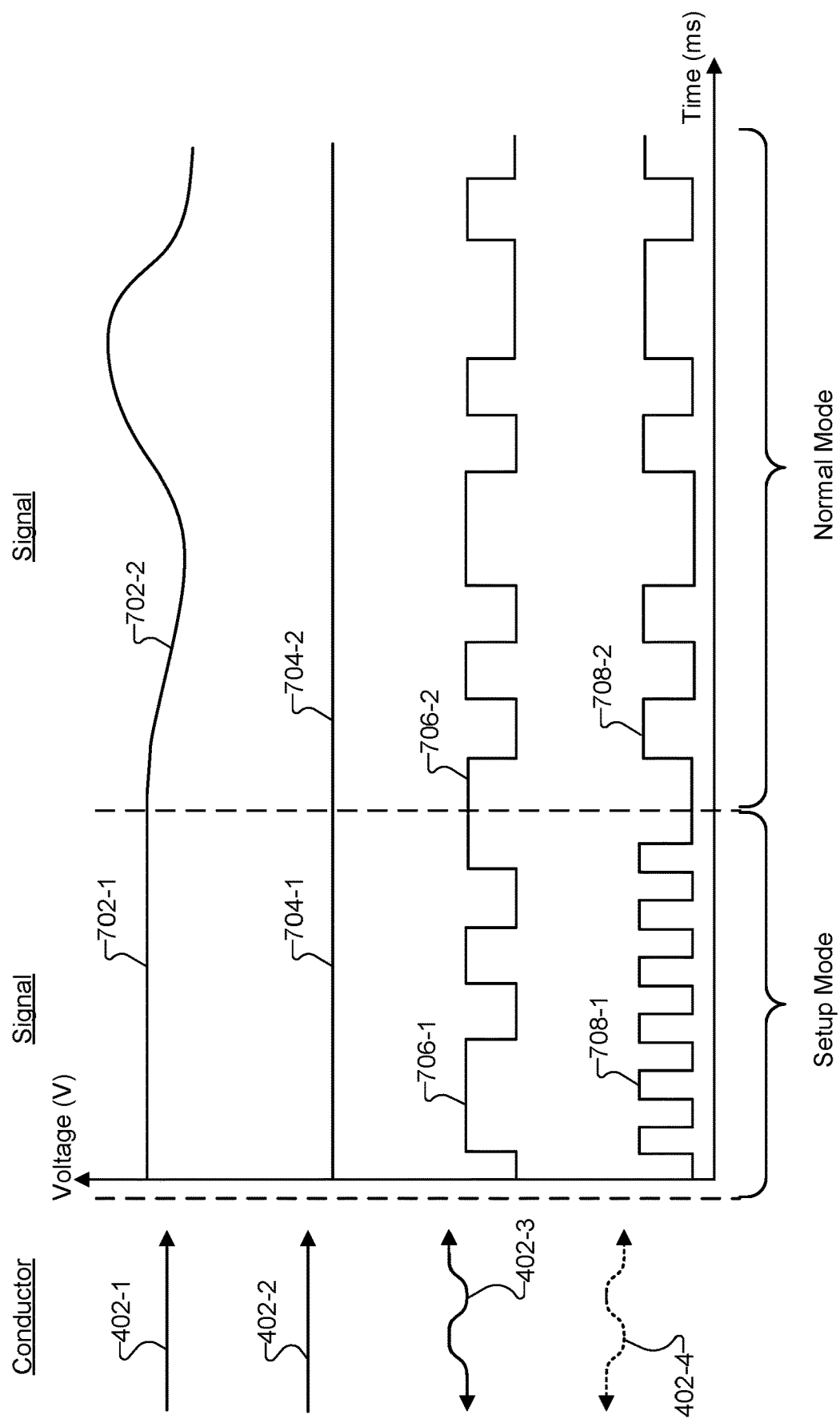
FIG. 7 illustrates exemplary waveforms that may be transmitted in the configuration of FIG. 6 when the active headpiece is operating in different exemplary modes of operation according to principles described herein.

To illustrate, FIG. 7 shows exemplary waveforms that may be transmitted on conductors 402 in configuration 600 when active headpiece 300 is operating in different exemplary modes of operation. Specifically, each conductor 402-1 through 402-4 is shown along a vertical axis next to a respective pair of waveforms depicting an exemplary voltage of the conductor with respect to time during a setup mode of operation (waveforms ending in "-1") and during a normal mode of operation (waveforms ending in "-2").

For example, waveform 702-1 illustrates a voltage with respect to time for conductor 402-1 during the setup mode of operation, while waveform 702-2 illustrates a voltage with respect to time for conductor 402-1 during the normal mode of operation. Similarly, waveform 704-1 illustrates a voltage with respect to time for conductor 402-2 during the setup mode of operation, while waveform 704-2 illustrates a voltage with respect to time for conductor 402-2 during the normal mode of operation. Waveform 706-1 illustrates a voltage with respect to time for conductor 402-3 during the setup mode of operation, while waveform 706-2 illustrates a voltage with respect to time for conductor 402-3 during the normal mode of operation. Waveform 708-1 illustrates a voltage with respect to time for conductor 402-4 during the setup mode of operation, while waveform 708-2 illustrates a voltage with respect to time for conductor 402-4 during the normal mode of operation.

Active headpiece 300 is configured to operate in one mode of operation at a time from a plurality of supported modes of operation including, without limitation, the setup mode of operation and the normal mode of operation illustrated in FIG. 7.

In the setup mode of operation, interface assembly 304 of active headpiece 300 may receive DC power by way of conductors 402-1 and 402-2 (conductor 402-2 serving as a ground reference for the voltage on conductor 402-1), a setup data signal by way of conductor 402-3, and a setup clock signal by way of conductor 402-4. Thus, as shown, waveform 702-1 may represent a fixed DC voltage (e.g., 1.0 V), waveform 704-1 may represent a fixed ground reference (i.e., at 0 V), and waveform 706-1 may represent a setup data signal that is toggling with respect to waveform 708-1, which may represent a setup clock signal. Even though, as described above, conductors 402-3 and 402-4 may be length-matched, combined in a twisted pair, or otherwise configured to carry differential signals, FIG. 7 illustrates that, in the setup mode of operation, the setup data and clock signals carried by these conductors may be implemented as two single-ended signals, rather than as a single differential signal. As such, while operating in the setup mode of operation, active headpiece 300 may perform one or more system setup operations based on the setup data signal and the setup clock signal, rather than, for example, performing the operations of recovering of the data signal and the clock signal from a self-clocking differential signal, generating first and second synthesized clock signals, wireless transmitting AC power and data-modulated AC signals, and so forth as described above.

For example, the one or more system setup operations performed in the setup mode of operation may include register configuration operations to setup clock control loop circuits (e.g., clock control loops 514) to properly generate the first and second synthesized clock signals to generate desired carrier frequencies during the normal mode of operation. As another example, the one or more system setup operations may include data reading operations and/or data writing operations to retrieve and/or store data to data storage facility 510. For example, if data storage facility 510 is implemented in integrated data storage within ASIC 404, the system setup operations may involve reading from and/or writing to the integrated data storage. Conversely, if data storage facility 510 is implemented in data storage external to ASIC 404, the system setup operations may involve reading from and/or writing to the external data storage.

In the normal mode of operation, interface assembly 304 of active headpiece 300 may receive DC power by way of conductors 402-1 and 402-2 (conductor 402-2 serving as a ground reference for the voltage on conductor 402-1), and a self-clocking differential signal by way of conductors 402-3 and 402-4. Thus, as shown in FIG. 7, waveform 702-2 may represent a variable DC voltage (e.g., ranging from 0.5 V to 3.0 V as the intensity of sound in the environment changes), waveform 704-2 may represent a fixed ground reference (i.e., at 0 V), and waveforms 706-2 and 708-2 may collectively represent the self-clocking differential signal comprising the data signal encoded with the clock signal at the clock frequency. Accordingly, as shown, waveforms 706-2 and 708-2 represent a differential signal in which the voltage on each conductor is always at a voltage level opposite the voltage level on the other conductor. As such, while operating in the normal mode of operation, active headpiece 300 may perform the recovery of the data signal and the clock signal from the self-clocking differential signal, the generation of the first and second synthesized clock signals, the wireless transmission of the AC power and the data-modulated AC signal, and so forth as has been described.

It will be understood that the waveforms in FIG. 7 are not drawn to scale. For example, the varying of the voltage on waveform 702-2 may occur on a much larger time scale than the toggling of the differential signal represented by waveforms 706-2 and 708-2.

Active headpiece 300 may operate within the setup mode or the normal mode at any point in time as may serve a particular implementation. For instance, in some implementations, active headpiece 300 may operate within the setup mode for a few milliseconds right when the cochlear implant system is powering up and/or when the cochlear implant system is powering down, while operating in the normal mode the remainder of the time the cochlear implant system is powered on.

Returning to FIG. 6, along with the 4-conductor interface between sound processor 602 and active headpiece 300 described above, configuration 600 further illustrates a wireless, transcutaneous interface between active headpiece 300 and cochlear implant 604. Specifically, wireless AC power 608 and a data-modulated wireless AC signal 610 may be transmitted through the skin from active headpiece 300 to cochlear implant 604, while a back-telemetry AC signal 612 may be transmitted through the skin from cochlear implant 604 back to active headpiece 300. These signals may be generated and transmitted via one or more coil antennas in any of the ways described herein.

Exemplary waveforms that illustrate the shape of wireless AC power 608, data-modulated wireless AC signal 610, and back-telemetry AC signal 612 are broken out from each signal in FIG. 6. In particular, these waveforms illustrate wireless AC power 608, data-modulated wireless AC signal 610, and back-telemetry AC signal 612 as implemented when the cochlear implant system is operating in the normal mode of operation. Each of wireless AC power 608, data-modulated wireless AC signal 610, and back-telemetry AC signal 612 may be implemented as RF signals having carrier frequencies in the RF band of the electromagnetic spectrum.

As shown, wireless AC power 608 may have a relatively low frequency and a relatively stable magnitude. As described above, this low frequency and consistency may allow power to be transmitted more efficiently than if power were modulated with data so as to cause the signal to constantly start and stop (e.g., as illustrated for data-modulated wireless AC signal 610). While, over a short period of time, wireless AC power 608 may appear to have a constant, fixed amplitude, it will be understood that the amplitude may vary over time in accordance with the variance of sound intensity in the environment and the resultant DC voltage level provided by sound processor 602 on conductors 402-1 and 402-2, as described above.

As further shown in FIG. 6, data-modulated wireless AC signal 610 may be transmitted using a higher carrier frequency than wireless AC power 608 for the reasons described above. Data may be modulated onto the signal in any suitable manner. For example, active headpiece 300 may be configured to wirelessly transmit the data-modulated wireless AC signal 610 using an on-off keying ("OOK") modulation technique. This technique, as illustrated in FIG. 6, may include modulating data bits onto the signal by switching the carrier frequency completely on (e.g., for '1' data bit) and off (e.g., for a '0' data bit). In other examples, data may be modulated in other ways such as by amplitude shift keying in which the signal is not switched fully on and off, but rather reduced and increased to two different non-zero levels. Because power is transmitted separately on wireless AC power 608, data-modulated wireless AC signal 610 may have a relatively small amplitude so as to be transmitted as efficiently as possible.

As further shown in FIG. 6, active headpiece 300 may be further configured to wirelessly receive, from cochlear implant 604, back-telemetry AC signal 612. For example, back-telemetry AC signal 612 may be implemented as an additional data-modulated wireless AC signal (e.g., similar to data-modulated wireless AC signal 610) upon which back-telemetry data is modulated. In some examples, rather than a data-modulated signal, back-telemetry data may involve more basic feedback such as a simple acknowledge (ACK) or non-acknowledge (NACK) flag. Active headpiece 300 may provide the data received by way of back-telemetry AC signal 612 to sound processor 602 in any suitable manner and/or over any conductor as may serve a particular implementation. For instance, the back-telemetry data may be transmitted over conductors 402-1 and 402-2, over an additional conductor dedicated to back-telemetry data (not explicitly shown), or over any other suitable conductor.

Figure 8:
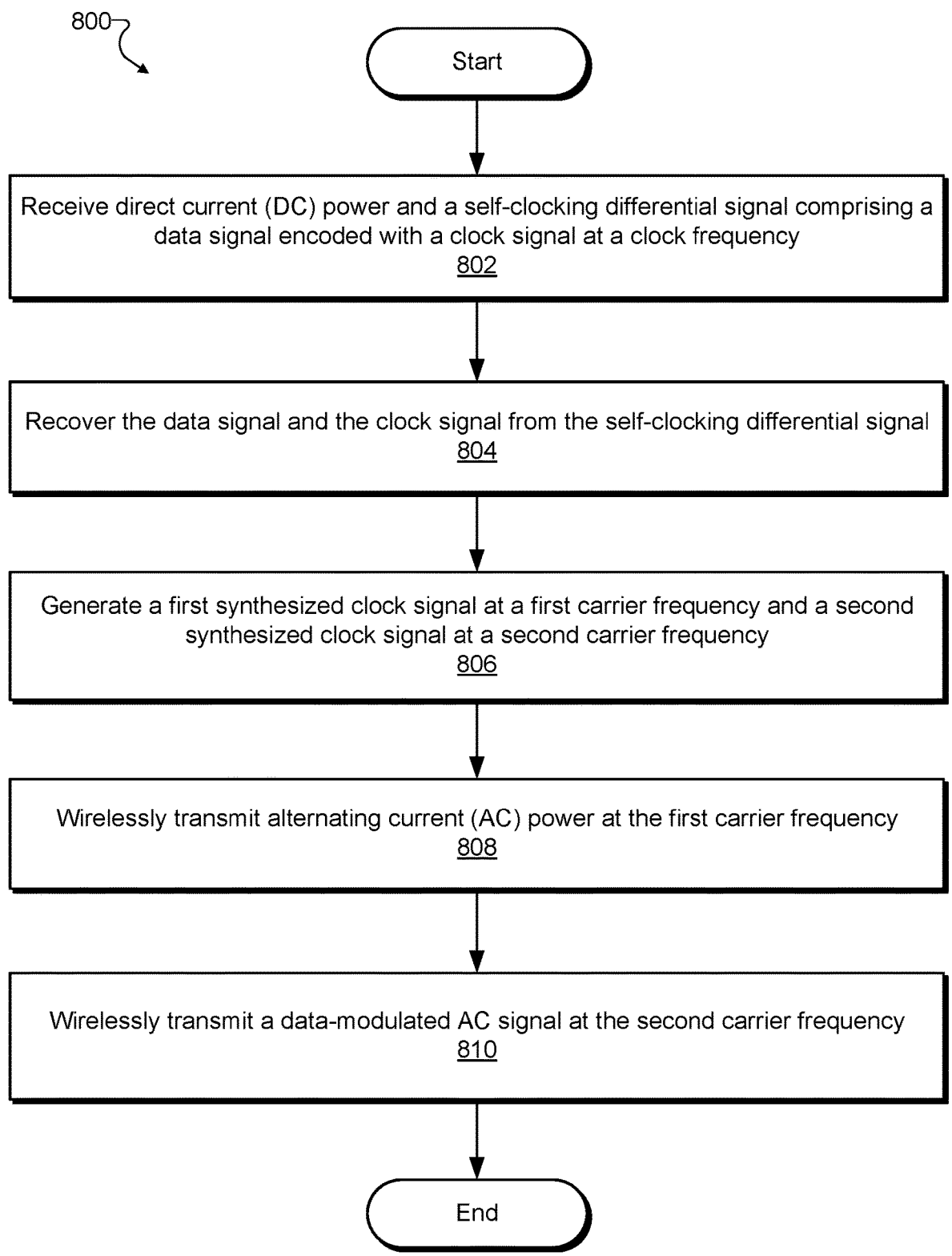
FIG. 8 illustrates an exemplary method for wirelessly transmitting power and data from an active headpiece to a cochlear implant according to principles described herein.

FIG. 8 illustrates an exemplary method 800 for wirelessly transmitting power and data from an active headpiece to a cochlear implant. While FIG. 8 illustrates exemplary operations according to one embodiment, other embodiments may omit, add to, reorder, and/or modify any of the operations shown in FIG. 8. In some examples, some or all of the operations shown in FIG. 8 may be performed by an active headpiece such as active headpiece 300 or an implementation thereof.

In operation 802, a headpiece included within a cochlear implant system associated with a patient may receive DC power and a self-clocking differential signal. For example, the headpiece may receive the DC power and the self-clocking differential signal from a sound processor included within the cochlear implant system and housed separately from the headpiece. The self-clocking differential signal may comprise a data signal encoded with a clock signal at a clock frequency. The data signal may be representative of data configured for use by a cochlear implant included within the cochlear implant system and implanted within the patient. Operation 802 may be performed in any of the ways described herein.

In operation 804, the headpiece may recover the data signal and the clock signal from the self-clocking differential signal received in operation 802. Specifically, the headpiece may recover the clock signal at the clock frequency. Operation 804 may be performed in any of the ways described herein.

In operation 806, the headpiece may generate a first synthesized clock signal at a first carrier frequency and a second synthesized clock signal at a second carrier frequency. For example, the headpiece may generate the first and second synthesized clock signals based on the clock signal at the clock frequency that was recovered in operation 804. In certain examples, at least one of the first and second carrier frequencies of the synthesized clock signals generated in operation 806 may be distinct from the clock frequency of the clock signal recovered in operation 804. Operation 806 may be performed in any of the ways described herein.

In operation 808, the headpiece may wirelessly transmit AC power to the cochlear implant based on the DC power received as part of operation 802. Specifically, the headpiece may wirelessly transmit the AC power at the first carrier frequency of the first synthesized clock signal generated in operation 806. Operation 808 may be performed in any of the ways described herein.

In operation 810, the headpiece may wirelessly transmit a data-modulated AC signal to the cochlear implant based on the data signal recovered as part of operation 804. Specifically, the headpiece may wirelessly transmit the data-modulated AC signal at the second carrier frequency of the second synthesized clock signal generated in operation 806. Operation 810 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
    an interface assembly configured to
        receive direct current (DC) power, and
        receive a self-clocking differential signal comprising a data signal encoded with a clock signal at a clock frequency; and
    electronic circuitry configured to
        recover, from the self-clocking differential signal, the data signal and the clock signal at the clock frequency,
        generate, based on the recovered clock signal at the clock frequency, a first synthesized clock signal at a first carrier frequency and a second synthesized clock signal at a second carrier frequency,
        wirelessly transmit, to an implantable stimulator implanted within a patient and based on the DC power, alternating current (AC) power at the first carrier frequency, and
        wirelessly transmit, to the implantable stimulator and based on the recovered data signal, a data-modulated AC signal at the second carrier frequency.

2. The system of claim 1, further comprising a housing within which the interface assembly and the electronic circuitry are disposed; and
    wherein:
        the interface assembly is communicatively coupled, by way of a cable, to a sound processor external to the patient and to the housing; and
        the interface assembly is configured to receive the DC power and the self-clocking differential signal from the sound processor by way of the cable.

3. The system of claim 1, implemented as a headpiece included within a cochlear implant system associated with the patient, wherein:
the implantable stimulator is implemented as a cochlear implant included within the cochlear implant system;
the data signal is representative of data configured for use by the cochlear implant; and
the electronic circuitry is configured to wirelessly transmit the AC power and the data-modulated AC signal transcutaneously to the cochlear implant while the cochlear implant is implanted within the patient.

4. The system of claim 1, wherein the second carrier frequency at which the electronic circuitry is configured to generate the second synthesized clock signal is at least twice as twice as high as the first carrier frequency at which the electronic circuitry is configured to generate the first synthesized clock signal.

5. The system of claim 1, wherein the system is configured to operate in one mode of operation at a time from a plurality of supported modes of operation including:
a normal mode of operation in which
the interface assembly receives the DC power by way of a first conductor within a cable and receives the self-clocking differential signal by way of a second conductor and a third conductor within the cable, and
the electronic circuitry performs the recovery of the data signal and the clock signal, the generation of the first and second synthesized clock signals, the wireless transmission of the AC power, and the wireless transmission of the data-modulated AC signal; and
a setup mode of operation in which
the interface assembly receives the DC power by way of the first conductor, receives a setup data signal by way of the second conductor, and receives a setup clock signal by way of the third conductor, and
rather than performing the recovery of the data signal and the clock signal, the generation of the first and second synthesized clock signals, the wireless transmission of the AC power, and the wireless transmission of the data-modulated AC signal, the electronic circuitry performs one or more system setup operations based on the setup data signal and the setup clock signal.

6. The system of claim 5, wherein:
the electronic circuitry includes a first clock control loop circuit configured to perform the generating of the first synthesized clock signal and a second clock control loop circuit configured to perform the generating of the second synthesized clock signal; and
the one or more system setup operations performed by the electronic circuitry in the setup mode of operation include register configuration operations to set up the first clock control loop circuit to generate the first synthesized clock signal at the first carrier frequency, and to set up the second clock control loop circuit to generate the second synthesized clock signal at the second carrier frequency.

7. The system of claim 1, further comprising a single antenna coil, and wherein:
the electronic circuitry wirelessly transmits the AC power to the implantable stimulator at the first carrier frequency by way of the single antenna coil; and
the electronic circuitry wirelessly transmits the data-modulated AC signal to the implantable stimulator at the second carrier frequency further by way of the single antenna coil.

8. The system of claim 1, further comprising:
a first antenna coil, and
a second antenna coil distinct from the first antenna coil; and wherein:
the electronic circuitry wirelessly transmits the AC power to the implantable stimulator at the first carrier frequency by way of the first antenna coil; and
the electronic circuitry wirelessly transmits the data-modulated AC signal to the implantable stimulator at the second carrier frequency by way of the second antenna coil.

9. The system of claim 1, further comprising:
a housing within which the interface assembly and the electronic circuitry are disposed; and
a microphone communicatively coupled, by way of a cable, to a sound processor external to the patient and to the housing;
wherein:
the microphone is configured to detect sound presented to the patient and to generate and provide, to the sound processor, a signal representative of the sound, and
the data signal is generated by the sound processor based on the signal representative of the sound.

10. The system of claim 1, wherein the electronic circuitry is further configured to:
access a fixed DC power having a voltage that is fixed at a particular level by deriving the fixed DC power from the received DC power or by recovering the fixed DC power from the self-clocking differential signal; and
use the fixed DC power to perform the recovery of the data signal and the clock signal and to perform the generation of the first and second synthesized clock signals.

11. The system of claim 1, wherein:
the data signal is encoded with the clock signal at the clock frequency using a Manchester clock encoding technique or using a biphase-mark clock encoding technique; and
the electronic circuitry is configured to recover the data signal and the clock signal in accordance with the Manchester clock encoding technique or the biphase-mark clock encoding technique.

12. The system of claim 1, implemented as a headpiece included within a cochlear implant system, the headpiece configured to be powered exclusively by power received from a sound processor included within the cochlear implant system such that no battery is disposed within the headpiece.

13. The system of claim 1, wherein the electronic circuitry is configured to wirelessly transmit the data-modulated AC signal using an on-off keying modulation technique.

14. The system of claim 1, wherein the electronic circuitry is further configured to wirelessly receive, from the implantable stimulator to which the electronic circuitry wirelessly transmits the AC power and the data-modulated AC signal, an additional data-modulated AC signal upon which back-telemetry data is modulated.

15. An application-specific integrated circuit (ASIC) configured to:
receive direct current (DC) power and a self-clocking differential signal comprising a data signal encoded with a clock signal at a clock frequency;
recover, from the self-clocking differential signal, the data signal and the clock signal at the clock frequency;
generate, based on the recovered clock signal at the clock frequency, a first synthesized clock signal at a first carrier frequency and a second synthesized clock signal at a second carrier frequency;
wirelessly transmit, to an implantable stimulator implemented within a patient and based on the DC power, alternating current (AC) power at the first carrier frequency; and wirelessly transmit, to the implantable stimulator and based on the recovered data signal, a data-modulated AC signal at the second carrier frequency.

16. The ASIC of claim 15, wherein the second carrier frequency at which the ASIC is configured to generate the second synthesized clock signal is at least twice as twice as high as the first carrier frequency at which the ASIC is configured to generate the first synthesized clock signal.

17. The ASIC of claim 15, wherein the ASIC is configured to operate in one mode of operation at a time from a plurality of supported modes of operation including:
a normal mode of operation in which the ASIC is configured to
perform the receiving of the DC power by way of a first input pin and the receiving of the self-clocking differential signal by way of a second input pin and a third input pin, and
perform the recovery of the data signal and the clock signal, the generation of the first and second synthesized clock signals, the wireless transmission of the AC power, and the wireless transmission of the data-modulated AC signal; and
a setup mode of operation in which the ASIC is configured to
perform the receiving of the DC power by way of the first input pin,
receive a setup data signal by way of the second input pin
receive a setup clock signal by way of the third input pin, and
perform one or more system setup operations based on the setup data signal and the setup clock signal, rather than performing the recovery of the data signal and the clock signal, the generation of the first and second synthesized clock signals, the wireless transmission of the AC power, and the wireless transmission of the data-modulated AC signal.

18. The ASIC of claim 17, wherein:
the ASIC includes a data storage interface configured to communicatively couple the ASIC with an external data storage device; and
the one or more system setup operations configured to be performed by the ASIC in the setup mode of operation include read and write operations to the external data storage device by way of the data storage interface.

19. The ASIC of claim 17, wherein:
the ASIC includes integrated data storage space; and
the one or more system setup operations configured to be performed by the ASIC in the setup mode of operation include read and write operations to the integrated data storage space.

20. A method comprising:
receiving direct current (DC) power and a self-clocking differential signal comprising a data signal encoded with a clock signal at a clock frequency;
recovering, from the self-clocking differential signal, the data signal and the clock signal at the clock frequency;
generating, based on the recovered clock signal at the clock frequency, a first synthesized clock signal at a first carrier frequency and a second synthesized clock signal at a second carrier frequency;
wirelessly transmitting, to an implantable stimulator implanted within a patient and based on the DC power, alternating current (AC) power at the first carrier frequency; and
wirelessly transmitting, to the implantable stimulator and based on the recovered data signal, a data-modulated AC signal at the second carrier frequency.

* * * * *